United States Patent
Sekiya et al.

(10) Patent No.: US 12,222,314 B2
(45) Date of Patent: Feb. 11, 2025

(54) SENSOR ELEMENT OF NOx SENSOR

(71) Applicant: NGK Insulators, Ltd., Nagoya (JP)

(72) Inventors: Takayuki Sekiya, Nisshin (JP); Yusuke Watanabe, Nagoya (JP); Shiho Iwai, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 441 days.

(21) Appl. No.: 17/577,426

(22) Filed: Jan. 18, 2022

(65) Prior Publication Data

US 2022/0236212 A1    Jul. 28, 2022

(30) Foreign Application Priority Data

Jan. 22, 2021 (JP) .................................. 2021-008725
Jan. 11, 2022 (JP) .................................. 2022-002293

(51) Int. Cl.
*G01N 27/41* (2006.01)
*G01N 27/406* (2006.01)
(Continued)

(52) U.S. Cl.
CPC ......... *G01N 27/409* (2013.01); *G01N 27/406* (2013.01); *G01N 27/4071* (2013.01);
(Continued)

(58) Field of Classification Search
CPC .. G01N 27/409; G01N 27/4077; G01N 27/41; G01N 27/417; G01N 33/0037;
(Continued)

(56) References Cited

U.S. PATENT DOCUMENTS

2003/0201171 A1    10/2003   Nakagaki et al.
2018/0172625 A1*    6/2018   Ichikawa ........... G01N 27/4075
(Continued)

FOREIGN PATENT DOCUMENTS

CN       107949785 A       4/2018
CN       110873748 A       3/2020
(Continued)

OTHER PUBLICATIONS

Sigma-Aldrich, Zirconium(IV) oxide-yttria stabilized (2024) (Year: 2024).*

(Continued)

*Primary Examiner* — James Lin
*Assistant Examiner* — Vivian A Tran
(74) *Attorney, Agent, or Firm* — MATTINGLY & MALUR, PC

(57) ABSTRACT

A sensor element includes: a base part containing an oxygen-ion conductive solid electrolyte as a constituent material; at least one internal space into which a measurement gas is introduced; and at least one pump cell including an internal electrode disposed to face the internal space, an out-of-space pump electrode disposed at a location other than the internal space, and a portion of the base part located between these electrodes, the internal electrode includes a noble metal, the solid electrolyte, and a pore, and, in the internal electrode, a degree of variation of a boundary of a first region formed of the base part or the solid electrolyte contiguous with the base part and a second region occupied by the noble metal and the pore in a thickness direction of the element is 0.5 μm or more and 6.5 μm or less.

6 Claims, 7 Drawing Sheets

(51) Int. Cl.
*G01N 27/407* (2006.01)
*G01N 27/409* (2006.01)
*G01N 27/417* (2006.01)
*G01N 33/00* (2006.01)

(52) U.S. Cl.
CPC ..... *G01N 27/4074* (2013.01); *G01N 27/4075* (2013.01); *G01N 27/4077* (2013.01); *G01N 27/41* (2013.01); *G01N 27/417* (2013.01); *G01N 33/0037* (2013.01)

(58) Field of Classification Search
CPC ............ G01N 27/406; G01N 27/4071; G01N 27/4073–4075
See application file for complete search history.

(56) References Cited

U.S. PATENT DOCUMENTS

| | | | |
|---|---|---|---|
| 2018/0202965 A1* | 7/2018 | Nakatou | G01N 27/41 |
| 2018/0259476 A1* | 9/2018 | Shimokawa | G01N 27/4071 |
| 2019/0004008 A1* | 1/2019 | Todo | G01N 27/4045 |
| 2019/0049404 A1* | 2/2019 | Ikeda | G01N 27/41 |
| 2020/0064302 A1 | 2/2020 | Sekiya et al. | |
| 2020/0072785 A1 | 3/2020 | Watanabe et al. | |
| 2020/0141896 A1* | 5/2020 | Namekata | G01N 27/4071 |
| 2020/0209184 A1* | 7/2020 | Ikeda | G01N 27/4071 |
| 2022/0214303 A1 | 7/2022 | Ito | |

FOREIGN PATENT DOCUMENTS

| | | | |
|---|---|---|---|
| DE | 112020003625 T5 * | 4/2022 | |
| EP | 0678740 B1 | 6/2001 | |
| JP | 2885336 B2 | 4/1999 | |
| JP | 2003-322634 A | 11/2003 | |
| JP | 2020-165866 A | 10/2020 | |
| WO | 2019/188613 A1 | 10/2019 | |
| WO | 2020/246174 A1 | 12/2020 | |

OTHER PUBLICATIONS

PubChem, Platinum (2024) (Year: 2024).*
Unexamined U.S. Appl. No. 17/577,423, filed Jan. 18, 2022.
Unexamined U.S. Appl. No. 17/577,425, filed Jan. 18, 2022.
Chinese Office Action received in corresponding Chinese Application No. 202210059660.1 dated Dec. 6, 2023.
Japanese Office Action received in corresponding Japanese Application No. 2022-002293 dated Jun. 4, 2024.

* cited by examiner

F I G. 7
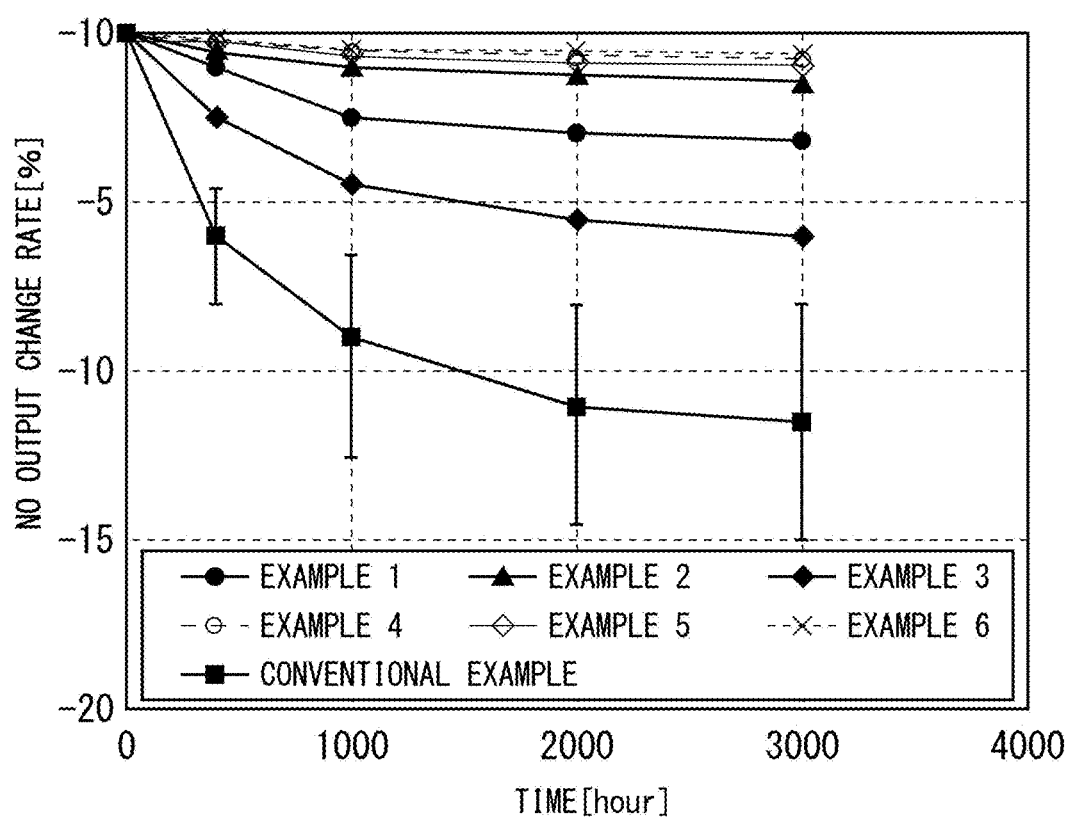

SENSOR ELEMENT OF NOx SENSOR

CROSS-REFERENCE TO RELATED APPLICATION

The present application claims priority from Japanese applications JP2021-008725, filed on Jan. 22, 2021 and JP2022-002293, filed on Jan. 11, 2022, the contents of which is hereby incorporated by reference into this application.

BACKGROUND OF THE INVENTION

Field of the Invention

The present invention relates to a sensor element of a limiting current NOx sensor, and, in particular, to a configuration of a measurement electrode of the sensor element.

Description of the Background Art

As a device for measuring the concentration of NOx in a measurement gas, such as a combustion gas and an exhaust gas from an internal combustion engine typified by an engine of a vehicle, a NOx sensor including a sensor element including a base formed of oxygen-ion conductive solid electrolyte ceramics, such as zirconia ($ZrO_2$), has been known (see Japanese Patent No. 2885336 and WO 2019/188613, for example).

The sensor element (a NOx sensor element) of the NOx sensor includes various electrodes (e.g., a pump electrode, a measurement electrode, and a reference electrode). These electrodes are porous cermet electrodes each formed of a composite material of a noble metal as a catalyst and zirconia as an electrolyte, and having a porous structure including many pores (cavities). As the catalytic noble metal, Pt and Pt with trace amounts of other substances (e.g., Rh and other noble metals) added are used. The NOx sensor element utilizes, at operation thereof, a catalytic reaction of the catalytic noble metal used for the electrodes and oxygen-ion conductivity of zirconia used for the base, and is thus used in a state of being heated to a relatively high sensor element driving temperature (600° C. to 900° C.).

The measurement gas, such as an exhaust gas from an engine, typically contains $O_2$. Thus, in a NOx sensor as disclosed in Japanese Patent No. 2885336 and WO 2019/188613, 02 in a measurement gas introduced into a NOx sensor element is first removed (separated from NOx) by an electrochemical pump cell of the NOx sensor element, NOx is then decomposed into $O_2$ and $N_2$ using a catalytic reaction of a measurement electrode, and a NOx concentration of the measurement gas is measured based on the magnitude of an oxygen-ion current flowing through a measurement pump cell in the decomposition.

When the measurement electrode is exposed to $O_2$, Pt and Pt/Rh of the electrode react with $O_2$ to generate oxides such as PtO, $PtO_2$, and $RhO_2$. When noble metals of the electrode decrease due to generation of the oxides, catalytic reactivity of the measurement electrode is reduced. These oxides have lower vapor pressure than Pt, and thus are likely to vaporize at a lower temperature than Pt. The vaporization leads to reduction in number of three-phase interfaces of a catalyst, an electrolyte, and a pore and two-phase interfaces of the catalyst and the electrolyte in the measurement electrode, and thus also causes reduction in catalytic reactivity of the measurement electrode.

As described above, oxygen is removed in advance from the measurement gas reaching the measurement electrode, but a small amount of oxygen still remains in the measurement gas. Furthermore, $O_2$ generated by decomposition of NOx might remain near the measurement electrode without promptly being ionized.

Thus, by continued use of the NOx sensor, NOx sensitivity is gradually reduced due to reduction in catalytic reactivity of the measurement electrode.

Elaborating on mass transfer near the measurement electrode at measurement, $O_2$ and NOx in the measurement gas having reached the measurement electrode first transfer through pores of the measurement electrode (referred to as a mass transfer process). When $O_2$ and NOx come into contact with a catalytic metal within the pores, Pt as a main component of the catalytic metal decomposes NO into $N_2$ and $O_2$, and further strips off an electron from $O_2$ to generate an oxygen ion. The generated oxygen ion is taken, at a two-phase interface of the catalyst and the electrolyte, from Pt into zirconia as the solid electrolyte, and transfers within zirconia due to a potential difference caused between the measurement electrode and an external electrode by application of a voltage by an external power supply (referred to as a charge transfer process).

If there are an oxygen ion not taken from the catalytic metal into zirconia and, further, oxygen before being ionized (generically referred to as surplus oxygen) in this process, however, the catalytic metal including Pt as the main component is oxidized by the surplus oxygen inside or at the surface of the electrode to generate PtO, $PtO_2$, and the like. These oxides gradually vaporize.

The inventors of the present invention have reasoned that reduction of the surplus oxygen not taken into zirconia can suppress vaporization of the oxides from the measurement electrode, and suppress reduction in sensitivity of the NOx sensor, and have conceived of the present invention through intense study.

WO 2019/188613 notes that, at oxidation of Pt in the measurement electrode, impurities present in the electrode further reduce a temperature at which the oxides vaporize, and discloses that vaporization of the oxides is suppressed by providing a gettering layer gettering such impurities. WO 2019/188613, however, neither discloses nor suggests suppression of vaporization of the oxides by reduction of the surplus oxygen.

SUMMARY

The present invention relates to a sensor element of a limiting current type NOx sensor, and is, in particular, directed to a configuration of a measurement electrode of the sensor element.

According to the present invention, a sensor element of a limiting current type NOx sensor includes: base part containing an oxygen-ion conductive solid electrolyte as a constituent material; at least one internal space into which a measurement gas is introduced; and at least one pump cell including an internal electrode disposed to face the at least one internal space, an out-of-space pump electrode disposed at a location other than the at least one internal space, and a portion of the base part located between the internal electrode and the out-of-space pump electrode, wherein the internal electrode includes a noble metal, the solid electrolyte, and a pore, and, in the internal electrode, a region boundary variation degree being a degree of variation of a boundary of a first region and a second region in a thickness direction of the element is 0.5 µm or more and 6.5 µm or less, the first region being formed of the base part or the solid electrolyte contiguous with the base part, the second region being occupied by the noble metal and the pore.

Deterioration of the measurement electrode due to the presence of surplus oxygen not taken into the measurement electrode is thereby suitably suppressed. A NOx sensor in which deterioration of measurement sensitivity is suitably suppressed even if the NOx sensor is used continuously is thereby achieved.

It is thus an object of the present invention to provide a NOx sensor in which reduction in sensitivity due to oxidation of a measurement electrode is suppressed even if the NOx sensor is used continuously.

These and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a graph showing results of a continuous drive test.

DESCRIPTION OF THE PREFERRED EMBODIMENTS

<General Configuration of Gas Sensor>

Figure 1:
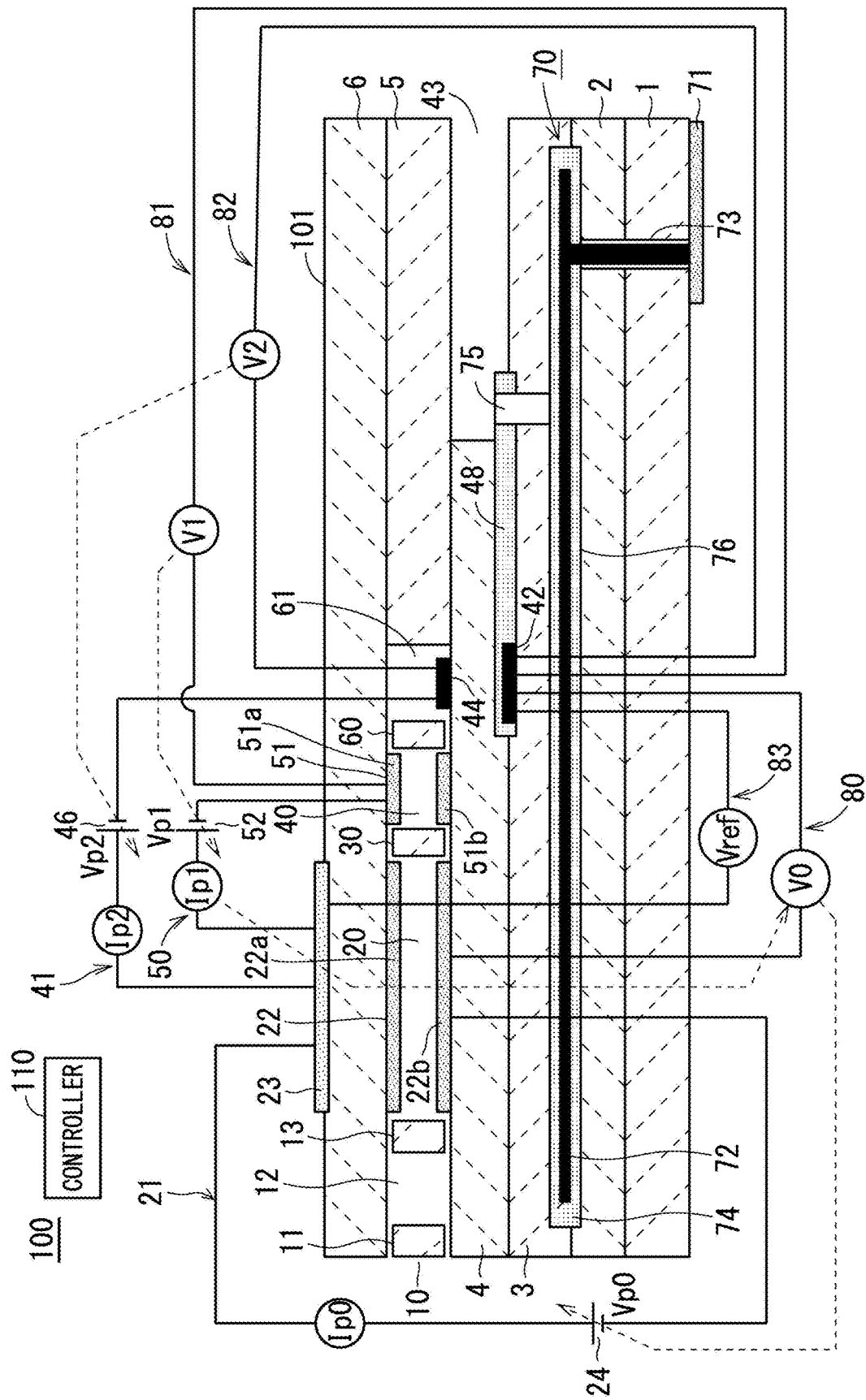
FIG. 1 is a diagram schematically showing one example of a configuration of a gas sensor 100.

FIG. 1 is a diagram schematically showing one example of a configuration of a gas sensor 100 according to an embodiment. The gas sensor 100 is a limiting current type NOx sensor sensing NOx and measuring the concentration thereof using a sensor element 101. The gas sensor 100 further includes a controller 110 controlling operation of each part and identifying the NOx concentration based on a NOx current flowing through the sensor element 101. FIG. 1 includes a vertical cross-sectional view taken along a longitudinal direction of the sensor element 101.

The sensor element 101 is a planar (elongated planar) element having a structure in which six solid electrolyte layers, namely, a first substrate layer 1, a second substrate layer 2, a third substrate layer 3, a first solid electrolyte layer 4, a spacer layer 5, and a second solid electrolyte layer 6 each formed of zirconia ($ZrO_2$) (e.g., yttria stabilized zirconia (YSZ)) as an oxygen-ion conductive solid electrolyte are laminated in the stated order from a bottom side of FIG. 1. The solid electrolyte forming these six layers is dense and airtight. A surface on an upper side and a surface on a lower side of each of these six layers in FIG. 1 are hereinafter also simply referred to as an upper surface and a lower surface, respectively. A part of the sensor element 101 formed of the solid electrolyte as a whole is generically referred to as a base part.

The sensor element 101 is manufactured, for example, by performing predetermined processing, printing of circuit patterns, and the like on ceramic green sheets corresponding to the respective layers, then laminating them, and further firing them for integration.

Between a lower surface of the second solid electrolyte layer 6 and an upper surface of the first solid electrolyte layer 4 in one leading end portion of the sensor element 101, a first diffusion control part 11 doubling as a gas inlet 10, a buffer space 12, a second diffusion control part 13, a first internal space 20, a third diffusion control part 30, a second internal space 40, a fourth diffusion control part 60, and a third internal space 61 are formed adjacent to each other to communicate in the stated order.

The buffer space 12, the first internal space 20, the second internal space 40, and the third internal space 61 are spaces (regions) inside the sensor element 101 looking as if they were provided by hollowing out the spacer layer 5, and having an upper portion, a lower portion, and a side portion respectively defined by the lower surface of the second solid electrolyte layer 6, the upper surface of the first solid electrolyte layer 4, and a side surface of the spacer layer 5. The gas inlet 10 may similarly look as if it was provided by hollowing out the spacer layer 5 at a leading end surface (at the left end in FIG. 1) of the sensor element 101 separately from the first diffusion control part 11. In this case, the first diffusion control part 11 is formed inside and adjacent to the gas inlet 10.

The first diffusion control part 11, the second diffusion control part 13, the third diffusion control part 30, and the fourth diffusion control part 60 are each provided as two horizontally long slits (whose openings have longitudinal directions perpendicular to the page of FIG. 1). A part extending from the gas inlet 10 to the third internal space 61 is also referred to as a gas distribution part.

At a location farther from the leading end than the gas distribution part is, a reference gas introduction space 43 having a side portion defined by a side surface of the first solid electrolyte layer 4 is provided between an upper surface of the third substrate layer 3 and a lower surface of the spacer layer 5. For example, air is introduced into the reference gas introduction space 43 as a reference gas at measurement of the NOx concentration.

An air introduction layer 48 is a layer formed of porous alumina, and the reference gas is introduced into the air introduction layer 48 through the reference gas introduction space 43. The air introduction layer 48 is formed to cover a reference electrode 42.

The reference electrode 42 is an electrode formed to be sandwiched between the upper surface of the third substrate layer 3 and the first solid electrolyte layer 4, and the air introduction layer 48 leading to the reference gas introduction space 43 is provided around the reference electrode 42 as described above. As will be described below, an oxygen concentration (oxygen partial pressure) in the first internal space 20 and the second internal space 40 can be measured using the reference electrode 42.

In the gas distribution part, the gas inlet 10 (first diffusion control part 11) is a part opening to an external space, and a measurement gas is taken from the external space into the sensor element 101 through the gas inlet 10.

The first diffusion control part 11 is a part providing predetermined diffusion resistance to the taken measurement gas.

The buffer space 12 is a space provided to guide the measurement gas introduced through the first diffusion control part 11 to the second diffusion control part 13.

The second diffusion control part 13 is a part providing predetermined diffusion resistance to the measurement gas introduced from the buffer space 12 into the first internal space 20.

In introducing the measurement gas from outside the sensor element 101 into the first internal space 20, the measurement gas having abruptly been taken into the sensor element 101 through the gas inlet 10 due to pressure fluctuations (pulsation of exhaust pressure in a case where the measurement gas is an exhaust gas of a vehicle) of the measurement gas in the external space is not directly introduced into the first internal space 20 but is introduced into the first internal space 20 after concentration fluctuations of the measurement gas are canceled through the first diffusion control part 11, the buffer space 12, and the second diffusion control part 13. This makes the concentration fluctuations of the measurement gas introduced into the first internal space 20 almost negligible.

The first internal space 20 is provided as a space to adjust oxygen partial pressure of the measurement gas introduced through the second diffusion control part 13. The oxygen partial pressure is adjusted by operation of a main pump cell 21.

The main pump cell 21 is an electrochemical pump cell including an inner pump electrode 22, an outer (out-of-space) pump electrode 23, and the second solid electrolyte layer 6 sandwiched between these electrodes. The inner pump electrode 22 has a ceiling electrode portion 22a provided on substantially the entire lower surface of a portion of the second solid electrolyte layer 6 facing the first internal space 20, and the outer pump electrode 23 is provided in a region, on an upper surface of the second solid electrolyte layer 6 (one main surface of the sensor element 101), corresponding to the ceiling electrode portion 22a to be exposed to the external space.

The inner pump electrode 22 is formed on upper and lower solid electrolyte layers (the second solid electrolyte layer 6 and the first solid electrolyte layer 4) defining the first internal space 20. Specifically, the ceiling electrode portion 22a is formed on the lower surface of the second solid electrolyte layer 6, which provides a ceiling surface to the first internal space 20, and a bottom electrode portion 22b is formed on the upper surface of the first solid electrolyte layer 4, which provides a bottom surface to the first internal space 20. The ceiling electrode portion 22a and the bottom electrode portion 22b are connected by a conducting portion (not illustrated) provided on a side wall surface (an inner surface) of the spacer layer 5 forming opposite side wall portions of the first internal space 20.

The ceiling electrode portion 22a and the bottom electrode portion 22b are provided to be rectangular in plan view. Only the ceiling electrode portion 22a or only the bottom electrode portion 22b may be provided.

The inner pump electrode 22 and the outer pump electrode 23 are each formed as a porous cermet electrode. In particular, the inner pump electrode 22 to be in contact with the measurement gas is formed using a material having a weakened reducing ability with respect to a NOx component in the measurement gas. For example, the inner pump electrode 22 is formed as a cermet electrode of an Au—Pt alloy containing Au of approximately 0.6 wt % to 1.4 wt % and $ZrO_2$ to have a porosity of 5% to 40% and a thickness of 5 μm to 20 μm. A weight ratio Pt:$ZrO_2$ of the Au—Pt alloy and $ZrO_2$ is only required to be approximately 7.0:3.0 to 5.0:5.0.

On the other hand, the outer pump electrode 23 is formed, for example, as a cermet electrode of Pt or an alloy thereof and $ZrO_2$ to be rectangular in plan view.

The main pump cell 21 can pump out oxygen in the first internal space 20 to the external space or pump in oxygen in the external space to the first internal space 20 by applying, from a variable power supply 24, a desired pump voltage Vp0 between the inner pump electrode 22 and the outer pump electrode 23 to allow a main pump current Ip0 to flow between the inner pump electrode 22 and the outer pump electrode 23 in a positive or negative direction. The pump voltage Vp0 applied between the inner pump electrode 22 and the outer pump electrode 23 in the main pump cell 21 is also referred to as a main pump voltage Vp0.

To detect the oxygen concentration (oxygen partial pressure) in an atmosphere in the first internal space 20, the inner pump electrode 22, the second solid electrolyte layer 6, the spacer layer 5, the first solid electrolyte layer 4, the third substrate layer 3, and the reference electrode 42 constitute a main sensor cell 80 as an electrochemical sensor cell.

The oxygen concentration (oxygen partial pressure) in the first internal space 20 can be known by measuring electromotive force V0 in the main sensor cell 80.

Furthermore, the controller 110 performs feedback control of the main pump voltage Vp0 so that the electromotive force V0 is constant, thereby to control the main pump current Ip0. The oxygen concentration in the first internal space 20 is thereby maintained at a predetermined constant value.

The third diffusion control part 30 is a part providing predetermined diffusion resistance to the measurement gas having an oxygen concentration (oxygen partial pressure) controlled by operation of the main pump cell 21 in the first internal space 20, and guiding the measurement gas to the second internal space 40.

The second internal space 40 is provided as a space to further adjust the oxygen partial pressure of the measurement gas introduced through the third diffusion control part 30. The oxygen partial pressure is adjusted by operation of an auxiliary pump cell 50. The oxygen concentration of the measurement gas is adjusted with higher accuracy in the second internal space 40.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40.

The auxiliary pump cell 50 is an auxiliary electrochemical pump cell including an auxiliary pump electrode 51, the outer pump electrode 23 (not limited to the outer pump electrode 23 and only required to be any appropriate electrode outside the sensor element 101), and the second solid electrolyte layer 6. The auxiliary pump electrode 51 has a ceiling electrode portion 51a provided on substantially the entire lower surface of a portion of the second solid electrolyte layer 6 facing the second internal space 40.

The auxiliary pump electrode 51 is provided in the second internal space 40 in a similar form to the inner pump electrode 22 provided in the first internal space 20 described previously. That is to say, the ceiling electrode portion 51a is formed on the second solid electrolyte layer 6, which provides a ceiling surface to the second internal space 40, and a bottom electrode portion 51b is formed on the first solid electrolyte layer 4, which provides a bottom surface to the second internal space 40. The ceiling electrode portion 51a and the bottom electrode portion 51b are rectangular in plan view, and are connected by a conducting portion (not illustrated) provided on the side wall surface (inner surface) of the spacer layer 5 forming opposite side wall portions of the second internal space 40.

As with the inner pump electrode 22, the auxiliary pump electrode 51 is formed using a material having a weakened reducing ability with respect to the NOx component in the measurement gas.

The auxiliary pump cell 50 can pump out oxygen in an atmosphere in the second internal space 40 to the external space or pump in oxygen in the external space to the second internal space 40 by applying a desired voltage (an auxiliary pump voltage) Vp1 between the auxiliary pump electrode 51 and the outer pump electrode 23 under control performed by the controller 110.

To control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an auxiliary sensor cell 81 as an electrochemical sensor cell.

The auxiliary pump cell 50 performs pumping using a variable power supply 52 whose voltage is controlled based on electromotive force V1 detected by the auxiliary sensor cell 81 in accordance with the oxygen partial pressure in the second internal space 40. The oxygen partial pressure in the atmosphere in the second internal space 40 is thereby controlled to a low partial pressure having substantially no effect on measurement of NOx.

At the same time, a resulting auxiliary pump current Ip1 is used to control the electromotive force in the main sensor cell 80. Specifically, the auxiliary pump current Ip1 is input, as a control signal, into the main sensor cell 80, and, through control of the electromotive force V0 therein, the oxygen partial pressure of the measurement gas introduced through the third diffusion control part 30 into the second internal space 40 is controlled to have a gradient that is always constant. In use as the NOx sensor, the oxygen concentration in the second internal space 40 is maintained at a constant value of approximately 0.001 ppm by the action of the main pump cell 21 and the auxiliary pump cell 50.

The fourth diffusion control part 60 is a part providing predetermined diffusion resistance to the measurement gas having an oxygen concentration (oxygen partial pressure) controlled by operation of the auxiliary pump cell 50 in the second internal space 40, and guiding the measurement gas to the third internal space 61.

The third internal space 61 is provided as a space to perform processing concerning measurement of the nitrogen oxide (NOx) concentration of the measurement gas introduced through the fourth diffusion control part 60. The NOx concentration is measured by operation of a measurement pump cell 41 in the third internal space 61. The measurement gas having the oxygen concentration adjusted with high accuracy in the second internal space 40 is introduced into the third internal space 61, so that the NOx concentration can be measured with high accuracy in the gas sensor 100.

The measurement pump cell 41 measures the NOx concentration of the measurement gas in the third internal space 61. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the third internal space 61 to be separated from the third diffusion control part 30.

The measurement electrode 44 is a porous cermet electrode of a noble metal and a solid electrolyte. For example, the measurement electrode 44 is formed as a cermet electrode of Pt or an alloy of Pt and another noble metal, such as Rh, and $ZrO_2$ as a constituent material for the sensor element 101. The measurement electrode 44 also functions as a NOx reduction catalyst to reduce NOx present in the atmosphere in the third internal space 61.

The measurement pump cell 41 can pump out oxygen generated through decomposition of NOx in an atmosphere around the measurement electrode 44, and detect the amount of generated oxygen as a pump current Ip2 under control performed by the controller 110.

In the present embodiment, the measurement electrode 44 has a two-layer configuration including a region where pores are not present and a region where pores are present. Details thereof will be described below.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute a measurement sensor cell 82 as an electrochemical sensor cell. A variable power supply 46 is controlled based on electromotive force V2 detected by the measurement sensor cell 82 in accordance with the oxygen partial pressure around the measurement electrode 44.

NOx in the measurement gas introduced into the third internal space 61 is reduced by the measurement electrode 44 ($2NO \rightarrow N_2 + O_2$) to generate oxygen. Oxygen as generated is to be pumped by the measurement pump cell 41, and, in this case, a voltage (measurement pump voltage) Vp2 of the variable power supply 46 is controlled so that the electromotive force V2 detected by the measurement sensor cell 82 is constant. The amount of oxygen generated around the measurement electrode 44 is proportional to the NOx concentration of the measurement gas, and thus the NOx concentration of the measurement gas is to be calculated using the pump current Ip2 in the measurement pump cell 41. The pump current Ip2 is hereinafter also referred to as a NOx current Ip2.

In the case that the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference air can be detected, and the concentration of the NOx component in the measurement gas can thereby be determined.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure of the measurement gas outside the sensor can be detected using electromotive force Vref obtained by the sensor cell 83.

The sensor element 101 further includes a heater part 70 playing a role in temperature adjustment of heating the sensor element 101 and maintaining the temperature thereof to enhance oxygen ion conductivity of the solid electrolyte forming the base part.

The heater part 70 mainly includes a heater electrode 71, a heater element 72, a heater lead 72a, a through hole 73, a heater insulating layer 74, and a heater resistance detection lead, which is not illustrated in FIG. 1. A portion of the heater part 70 other than the heater electrode 71 is buried in the base part of the sensor element 101.

The heater electrode 71 is an electrode formed to be in contact with a lower surface of the first substrate layer 1 (the other main surface of the sensor element 101).

The heater element 72 is a resistive heating element provided between the second substrate layer 2 and the third substrate layer 3. The heater element 72 generates heat by being powered from a heater power supply, which is not illustrated in FIG. 1, outside the sensor element 101 through the heater electrode 71, the through hole 73, and the heater lead 72a, which constitute a current-carrying path. The heater element 72 is formed of Pt, or contains Pt as a main component. The heater element 72 is buried, in a predetermined range of the sensor element 101 in which the gas distribution part is provided, to oppose the gas distribution part in a thickness direction of the element. The heater element 72 is provided to have a thickness of approximately 10 μm to 20 μm.

In the sensor element 101, each part of the sensor element 101 can be heated to a predetermined temperature and the temperature can be maintained by allowing a current to flow through the heater electrode 71 to the heater element 72 to thereby cause the heater element 72 to generate heat. Specifically, the sensor element 101 is heated so that the temperature of the solid electrolyte and the electrodes in the vicinity of the gas distribution part is approximately 700° C. to 900° C. The oxygen ion conductivity of the solid electrolyte forming the base part of the sensor element 101 is enhanced by the heating. A heating temperature of the heater element 72 when the gas sensor 100 is in use (when the sensor element 101 is driven) is referred to as a sensor element driving temperature.

A degree of heat generation (heater temperature) of the heater element 72 is grasped by the magnitude of a resistance value (heater resistance) of the heater element 72.

Although not illustrated in FIG. 1, a thermal shock resistant protective layer as a single- or multi-porous layer covering the sensor element 101 may further be provided outside in a predetermined range on a side of the one leading end portion (side of the left end in FIG. 1) of the sensor element 101. The thermal shock resistant protective layer is provided to prevent cracking of the sensor element 101 due to thermal shock caused by moisture contained in the measurement gas adhering to the sensor element 101 and condensing when the gas sensor 100 is in use, and prevent poisoning substances coexisting in the measurement gas from entering into the sensor element 101. A laminar gap (gap layer) may be formed between the sensor element 101 and the thermal shock resistant protective layer.

<Detailed Configuration of Measurement Electrode>

Figure 2:
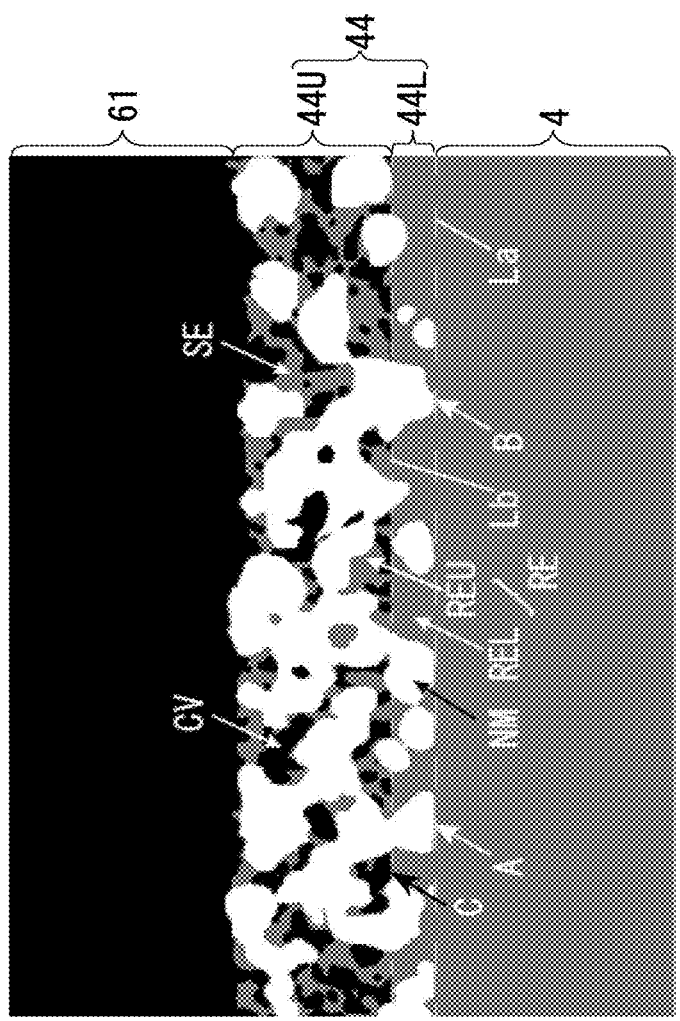
FIG. 2 is a model diagram showing a partial cross section of a measurement electrode 44 along a thickness direction of an element.

A configuration of the measurement electrode 44 of the sensor element 101 having a configuration as described above will be described in more detail next. FIG. 2 is a model diagram showing a partial cross section of the measurement electrode 44 along the thickness direction of the element. Dashed lines La and Lb shown in FIG. 2 are added for ease of understanding.

In FIG. 2, a portion below the dashed line La is the first solid electrolyte layer 4 formed of a solid electrolyte (zirconia), and the measurement electrode 44 is provided on the first solid electrolyte layer 4. A portion above the measurement electrode 44 is the third internal space 61 (more particularly, a portion of the third internal space 61 not occupied by the measurement electrode 44, but hereinafter simply referred to as the third internal space 61 for the sake of convenience).

As described above, the measurement electrode 44 is the porous cermet electrode of the noble metal, such as Pt and an alloy of Pt and Rh and the like, and the solid electrolyte (zirconia). Thus, as shown in FIG. 2, the measurement electrode 44 has a configuration that there coexist a portion formed of a noble metal NM of white in FIG. 2, a portion formed of a solid electrolyte SE of gray (or light gray) in FIG. 2, and a portion formed of a pore (cavity) CV of black (or dark gray) in FIG. 2. As with the solid electrolyte SE, the first solid electrolyte layer 4 is of gray in FIG. 2. This is because they are both formed of zirconia. The third internal space 61 is of black in FIG. 2 as with the pore CV, and this is because they are both spaces or gaps.

The measurement electrode 44 according to the present embodiment, however, does not have a configuration in which the three portions (phases) formed of the noble metal NM, the solid electrolyte SE, and the pore CV randomly coexist as a whole, but has a two-layer configuration including a lower layer (also referred to as a two-phase region) 44L where only the noble metal NM and the solid electrolyte SE randomly coexist, and the pore CV is not present and an upper layer (also referred to as a three-phase region) 44U where the noble metal NM, the solid electrolyte SE, and the pore CV randomly coexist. A boundary between the lower layer 44L and the upper layer 44U is shown in the dashed line Lb in FIG. 2.

Viewed another way, the dashed line La shows a lowermost end of a range in which the noble metal NM is present in a thickness direction of the measurement electrode 44, and the dashed line Lb shows a lowermost end of a range in which the pore CV is present in the thickness direction of the measurement electrode 44. Expressed yet another way, it can be said that the dashed line La is a boundary between a region where the noble metal NM is present and a region where the noble metal NM is not present in the thickness direction of the measurement electrode 44, and the dashed line Lb is a boundary between a region where the pore CV is present and a region where the pore CV is not present in the thickness direction of the measurement electrode 44.

A portion of the solid electrolyte SE forming the measurement electrode 44 contiguous with the base part formed of the solid electrolyte of the sensor element 101 (a portion contiguous with the base part beyond the dashed line La) is hereinafter particularly referred to as a contiguous region RE. Furthermore, a portion of the contiguous region RE belonging to the lower layer 44L (a portion located between the dashed line La and the dashed line Lb) is referred to as a lower contiguous region REL, and a portion of the contiguous region RE belonging to the upper layer 44U (a portion located between the dashed line Lb and the third internal space 61) is referred to as an upper contiguous region REU.

As described above, the measurement electrode 44 of the sensor element 101 according to the present embodiment is characterized in that the measurement electrode 44 as a whole is provided as the porous cermet electrode in which the noble metal NM, the solid electrolyte SE, and the pore CV coexist, but these three phases actually coexist only in the upper layer 44U provided on a side of an upper surface of the electrode, and a range below the upper layer 44U is the lower layer 44L having a two-phase configuration in which the pore CV is not present.

In other words, in the measurement electrode 44, the boundary (dashed line La) between the base part formed of the solid electrolyte (more particularly, the first solid electrolyte layer 4) and the measurement electrode 44 is different from the boundary (dashed line Lb) between the region where the pore CV is present and the region where the pore CV is not present.

<Example of Identification of Locations of Boundaries>

A way to identify locations of the respective boundaries (dashed lines La and Lb) when the locations of the boundaries are evaluated will be described next with an example, which are a location of the boundary of the region where the noble metal NM is present and the region where the noble metal NM is not present as the lowermost end of the range in which the noble metal NM is present and a location of the boundary of the region where the pore CV is present and the region where the pore CV is not present as the lowermost end of the range in which the pore CV is present in the thickness direction of the measurement electrode 44 having a configuration as described above.

First, a cross-sectional image of the measurement electrode 44 along the thickness direction as shown in FIG. 2 is captured using a scanning electron microscope (SEM) and the like, for example. In this case, an image capturing range is set so that the measurement electrode 44 is as horizontal as possible in the captured image, and the captured image includes at least the entire range in the thickness direction of the lower layer 44L of the measurement electrode 44 and a portion near the boundary between the measurement electrode 44 and the first solid electrolyte layer 4. Image capturing magnification is preferably approximately 500× to 1000× in view of the need to clearly identify each of interfaces among the three phases in the captured image. In this case, the cross-sectional image in a range of approximately 100 μm to 200 μm in the longitudinal direction of the element can be obtained.

Data of the obtained captured image is then analyzed based on a known image processing method to identify the ranges (all the pixels corresponding to the ranges) in which the noble metal NM, the solid electrolyte SE (and the first solid electrolyte layer 4), and the pore CV (and the third internal space 61) are present. In a case where the captured image is an SEM image, for example, which phases respective pixels of the captured image correspond to can be identified by a difference in brightness.

A coordinate point (pixel location) providing a location of a lowermost end of the noble metal NM in the captured image is then identified based on the data of the captured image. In a case of FIG. 2, a point A corresponds to the coordinate point. A straight line passing through the point A and being parallel to a horizontal direction of the captured image is to correspond to the dashed line La showing the lowermost end of the range in which the noble metal NM is present.

However, the measurement electrode 44 might be inclined to no small extent in the captured image, although the measurement electrode 44 is as horizontal as possible at image capturing. In light of the foregoing, the dashed line La showing the lowermost end of the range in which the noble metal NM is present may be set by identifying, from a range of the noble metal NM in the captured image, the coordinate point (e.g., the point A in FIG. 2) of the location of the lowermost end and a coordinate point (e.g., a point B in FIG. 2) at the second lowest location, correcting the captured image so that a straight line passing through the point A and the point B is horizontal, and determining the straight line passing through the point A and the point B in the corrected captured image as the dashed line La.

When the dashed line La is identified, a coordinate point (pixel location) providing a location of a lowermost end of the pore CV in the (corrected) captured image is then identified based on the data of the captured image. In a case of FIG. 2, a point C corresponds to the coordinate point. A straight line passing through the point C and being parallel to the horizontal direction of the captured image is to correspond to the dashed line Lb showing the lowermost end of the range in which the pore CV is present.

<Region Boundary Variation of Solid Electrolyte Region>

In the sensor element 101 according to the present embodiment, the contiguous region RE as a portion of the solid electrolyte SE forming the measurement electrode 44 is contiguous with the base part formed of the solid electrolyte as described above. The majority of the contiguous region RE is the lower contiguous region REL belonging to the lower layer 44L in which the pore is not present, while a portion of the contiguous region RE is the upper contiguous region REU further contiguous with the lower contiguous region REL and belonging to the upper layer 44U.

Since the pore CV is not present in the lower layer 44L, portions which are in a lower end portion of the lower layer 44L and in which the solid electrolyte SE is present constitute the contiguous region RE as a whole. The contiguous region RE is thus significantly formed in the sensor element 101 according to the present embodiment compared with a conventional sensor element in which the pore CV is present up to the lower end portion of the lower layer 44L.

Significant formation of the contiguous region RE in the measurement electrode 44 means that a boundary (hereinafter, also referred to as a region boundary) of a region formed of the solid electrolyte and contiguous upward from a side of the first solid electrolyte layer 4 in the thickness direction of the element (i.e., a region including the first solid electrolyte layer 4 and the contiguous region RE, hereinafter generically referred to as a first region) and a region occupied by the noble metal NM and the pore CV (hereinafter generically referred to as a second region) is not along the boundary of the first solid electrolyte layer 4 and the measurement electrode 44 (i.e., dashed line La), and varies significantly in the thickness direction of the element.

Figure 3:
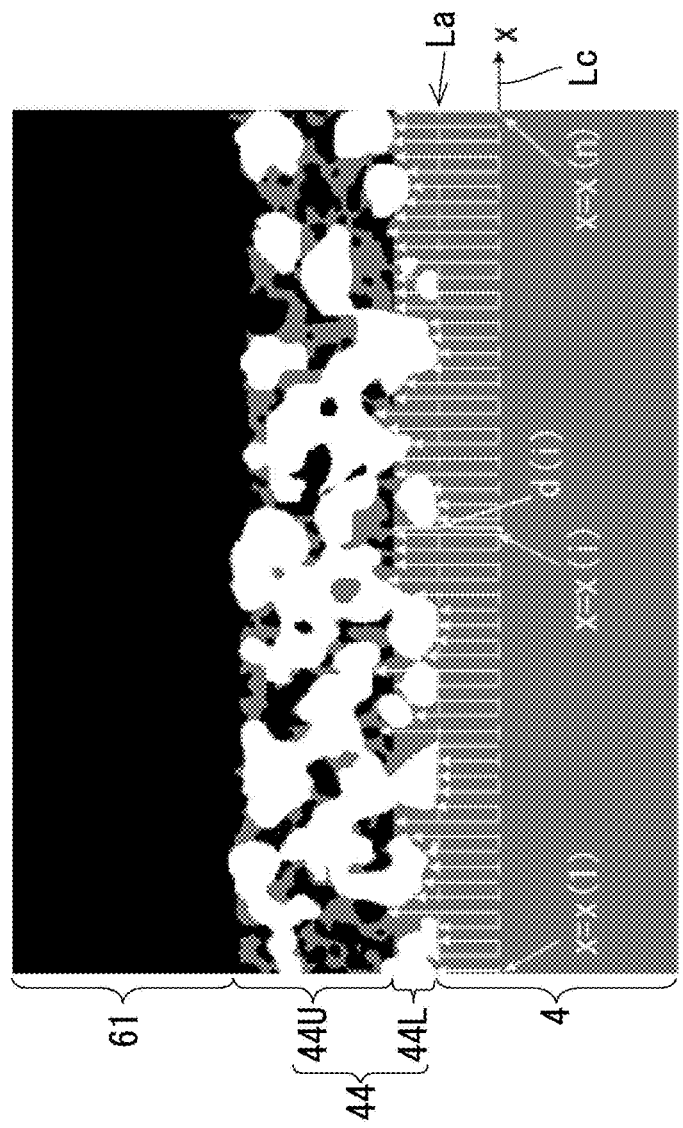
FIG. 3 is a diagram for describing a way to evaluate a region boundary variation degree being a degree of variation of a boundary of a first region and a second region in the thickness direction of the element.

FIG. 3 is a diagram for describing a way to evaluate a degree of variation of the boundary of the first region and the second region in the thickness direction of the element (hereinafter, region boundary variation degree) by taking, as an example, the model diagram showing the partial cross section of the measurement electrode 44 shown in FIG. 2.

As shown in FIG. 3, when a straight line Lc matching or being parallel to the dashed line La showing the lowermost end of the range in which the noble metal NM is present is set to an x-axis, and a straight line is extended from any point represented by an equation $x=x(i)$ on the x-axis as a starting point in the thickness direction of the element perpendicular to the dashed line La or the straight line Lc, one of the lower end of the noble metal NM and the lower end of the pore CV that the straight line reaches first is set to a region boundary point on the straight line. When the region boundary varies significantly in the thickness direction of the element, a length $d(i)$ of a line segment (shown as an arrow in FIG. 3) extending from the starting point to the region boundary tends to vary significantly with the location of the selected starting point. Since the pore CV is present only in the upper layer 44U, a portion in which the region boundary point is an intersection of the pore CV and the first region can be considered as a portion in which the first region has entered into the second region particularly significantly.

In light of the foregoing, when many starting points represented by an equation x=x(1) to x(n) are set at predetermined intervals along the straight line Lc, and region boundary points corresponding to the respective starting points are identified as shown in FIG. 3, the standard deviation σ of lengths d(1) to d(n) of line segments extending from the starting points to the respective region boundary points is indicative of the region boundary variation degree. That is to say, the boundary between the first region and the second region varies significantly in the thickness direction of the element when the standard deviation σ has a greater value, and the boundary between the first region and the second region is along the boundary (i.e., dashed line La) between the first solid electrolyte layer 4 and the measurement electrode 44 when the standard deviation σ has a value closer to zero.

In identifying the distance d(i), the noble metal NM completely surrounded by the solid electrolyte SE, and not in contact with the pore CV may be ignored. This is because the contiguous region RE is still present above the noble metal NM in the thickness direction of the element.

Although the straight line Lc is different from the dashed line La in FIG. 3, for convenience in description, they may match each other. This is because, although an average value of the distance d(i) varies with the location of the straight line Lc, the standard deviation σ does not depend on the location of the straight line Lc.

Although the starting points are set at discrete intervals in FIG. 3 for purposes of illustration, the starting points are actually preferably set at smaller intervals of 0.1 μm, for example.

Figure 4:
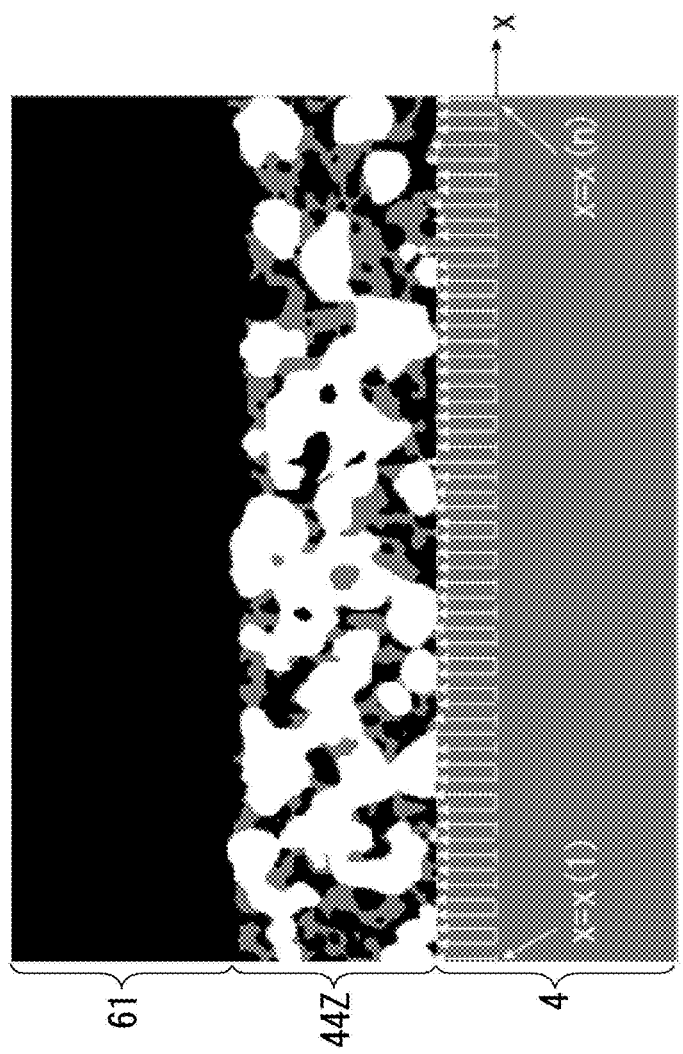
FIG. 4 is a model diagram of a partial cross section of a measurement electrode 44Z having a configuration in which three phases coexist in the electrode as a whole.

FIG. 4 is a model diagram showing a partial cross section of a measurement electrode 44Z having a configuration in which three phases randomly coexist in the electrode as a whole shown for comparison as a target for evaluation of the region boundary variation degree. A location at which the measurement electrode 44Z is disposed in the sensor element is the same as a location at which the measurement electrode 44 is disposed in the sensor element. A portion of white in FIG. 4 is the portion formed of the noble metal NM, a portion of gray in FIG. 4 is the portion formed of the solid electrolyte SE, and a portion of black in FIG. 4 is the portion formed of the pore CV also in the measurement electrode 44Z shown in FIG. 4.

In the measurement electrode 44Z, the boundary between the region where the pore CV is present and the region where the pore CV is not present generally matches the boundary between the base part formed of the solid electrolyte (more particularly, the first solid electrolyte layer 4) and the measurement electrode 44. That is to say, an appreciable portion of the base part is in contact with the pore CV or the noble metal NM. Although the contiguous region RE as a portion of the solid electrolyte SE contiguous with the base part is present, a degree of formation thereof is small as the pore CV is present.

Thus, in a case of FIG. 4, almost no difference can be seen among the lengths d(1) to d(n) of the line segments obtained as in a case of FIG. 3. The region boundary variation degree of the sensor element including the measurement electrode 44Z thus has a smaller value than the region boundary variation degree of the sensor element 101 including the measurement electrode 44 having the two-layer configuration.

This suggests that the region boundary variation degree has a value reflecting the configuration of the measurement electrode 44.

<Relationship between Configuration of Measurement Electrode and Suppression of Deterioration>

The measurement electrode 44 and the measurement electrode 44Z have a mass transfer process in the electrode in common. That is to say, NOx and trace amounts of $O_2$, which are contained in the measurement gas having reached the measurement electrode 44 or the measurement electrode 44Z disposed in the third internal space 61 from outside the element, transfer through the pore CV, and come into contact with the noble metal NM as a catalyst. Pt as a main component of the noble metal NM causes decomposition of NOx to generate $O_2$, and strips off an electron from $O_2$ to generate an oxygen ion. The generated oxygen ion is taken, at a two-phase interface of the noble metal NM and the solid electrolyte SE, from Pt into the solid electrolyte SE, and transfers within the sensor element 101 due to a potential difference caused between the measurement electrode 44 or the measurement electrode 44Z and the outer pump electrode 23 in the measurement pump cell 41.

In a case of the measurement electrode 44Z having a three-phase configuration as a whole and thus having a small value of the region boundary variation degree, however, the pore CV is present near or adjacent to the first solid electrolyte layer 4, and an interface of the solid electrolyte SE and the pore CV is present at a relatively high ratio, whereas an interface of the noble metal NM and the solid electrolyte SE is present at a relatively low ratio. Thus, surplus oxygen coming into contact with the noble metal but not taken into the solid electrolyte is likely to be generated, and thus deterioration of the measurement electrode caused by oxidation of the noble metal containing Pt as the main component by the surplus oxygen is likely to occur.

In contrast, in the case of the measurement electrode 44 including the lower layer 44L having the two-phase configuration and the upper layer 44U having the three-phase configuration, and thus having a large value of the region boundary variation degree, while the pore CV through which oxygen is distributed is present only in the upper layer 44U, the solid electrolyte SE present in the lower layer 44L is almost in the lower contiguous region REL contiguous with the base part, and is only in contact with the noble metal NM. Thus, the two-phase interface of the noble metal NM and the solid electrolyte SE is present at a higher ratio than that in a conventional gas sensor, and, in particular, only the two-phase interface is present in the lower layer 44L, so that the surplus oxygen is less likely to accumulate in the pore CV to be in contact with the noble metal NM, and deteriorate the measurement electrode 44.

That is to say, in the gas sensor 100 according to the present embodiment, deterioration of the measurement electrode 44 due to the presence of the surplus oxygen is suitably suppressed. Deterioration of measurement sensitivity is thus suitably suppressed even if the gas sensor 100 is used continuously.

The region boundary variation degree is preferably 0.5 μm or more and 6.5 μm or less.

In this case, the rate of change of the NOx current Ip2 with respect to an initial value thereof when the gas sensor 100 is used continuously is suppressed to 6% or less. That is to say, a rate of deterioration of measurement sensitivity when the gas sensor 100 is used continuously is suppressed to 6% or less.

The region boundary variation degree is more preferably 1 μm or more and 5 μm or less. In this case, the rate of change of the NOx current Ip2 with respect to the initial value thereof when the gas sensor 100 is used continuously, that is, the rate of deterioration of measurement sensitivity when the gas sensor 100 is used continuously is suppressed to approximately 3% or less. Furthermore, reduction in pumping capacity of the measurement pump cell 41 due to insufficiency of the number of sites for ionization of the measurement gas, which can be caused when a value of the region boundary variation degree is large and therefore there are few pores in the measurement electrode 44, is suppressed.

Furthermore, it is preferable that the measurement electrode 44 have a thickness of 10 μm to 30 μm, and a thickness ratio $t_U:t_L$ be in a range of 95:5 to 10:90. In other words, a ratio of a distance to from an uppermost portion of the measurement electrode 44 to the lowermost end (dashed line Lb) of the range in which the pore CV is present with respect to a distance $t_L$ from a lowermost portion of the measurement electrode 44 to the lowermost end of the range in which the pore CV is present is in the range of 95:5 to 10:90.

A volume ratio of the solid electrolyte SE in the upper layer 44U is 20% to 40%, and a volume ratio of the solid electrolyte SE in the lower layer 44L is 50% to 60%.

In addition, the configuration of the measurement electrode 44 in which the solid electrolyte contiguous with the first solid electrolyte layer 4 enters into a noble metal portion and which has a large value of the region boundary variation degree produces the so-called anchoring effect. The configuration of the measurement electrode 44 used in the gas sensor 100 according to the present embodiment is thus effective at suppressing separation of the measurement electrode 44.

<Process of Manufacturing Sensor Element>

A process of manufacturing the sensor element 101 having a configuration and features as described above will be described next. In the present embodiment, a laminated body including green sheets (also referred to as base material tapes) containing zirconia as a ceramic component is formed, and the laminated body is cut and fired to manufacture the sensor element 101.

Figure 5:
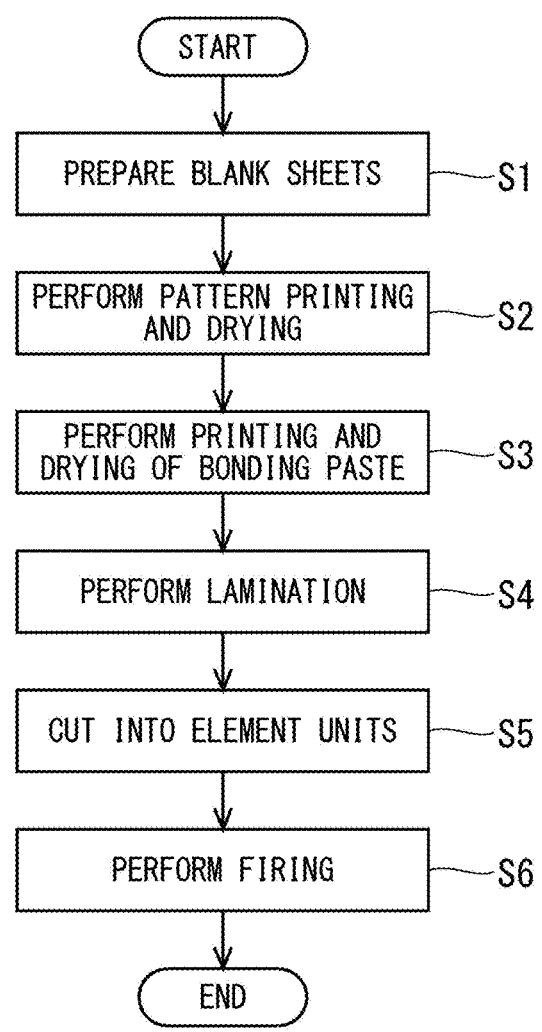
FIG. 5 is a flowchart of processing at manufacture of a sensor element 101.

Description will be made below by taking, as an example, a case where the sensor element 101 including the six layers shown in FIG. 1 is manufactured. In this case, six green sheets corresponding to the first substrate layer 1, the second substrate layer 2, the third substrate layer 3, the first solid electrolyte layer 4, the spacer layer 5, and the second solid electrolyte layer 6 are to be prepared. FIG. 5 is a flowchart of processing at the manufacture of the sensor element 101.

In a case where the sensor element 101 is manufactured, blank sheets (not illustrated) being green sheets having no pattern formed thereon are prepared first (step S1). In a case where the sensor element 101 including the six layers is manufactured, six blank sheets corresponding to the respective layers are prepared.

The blank sheets have a plurality of sheet holes used for positioning in printing and lamination. The sheet holes are formed to the blank sheets in advance prior to pattern formation through, for example, punching by a punching machine. Green sheets corresponding to layers in which an internal space is formed also include penetrating portions corresponding to the internal space formed in advance through, for example, punching as described above. The blank sheets corresponding to the respective layers of the sensor element 101 are not required to have the same thickness.

After preparation of the blank sheets corresponding to the respective layers, pattern printing and drying are performed on the individual blank sheets (step S2). Specifically, a pattern of various electrodes, a pattern of the heater element 72 and the heater insulating layer 74, a pattern of internal wiring, which is not illustrated, and the like are formed.

Application or placement of a sublimable material to form the first diffusion control part 11, the second diffusion control part 13, and the third diffusion control part 30 is also performed at the time of pattern printing.

The patterns are printed by applying pastes for pattern formation prepared in accordance with the properties required for respective formation targets onto the blank sheets using known screen printing technology. A known drying means can be used for drying after printing.

A method different from a conventional method is used to form, from among these patterns, a pattern to eventually be the measurement electrode 44. In this regard, description will be made below.

After pattern printing on each of the blank sheets, printing and drying of a bonding paste are performed to laminate and bond the green sheets corresponding to the respective layers (step S3). The known screen printing technology can be used for printing of the bonding paste, and the known drying means can be used for drying after printing.

The green sheets to which an adhesive has been applied are then stacked in a predetermined order, and the stacked green sheets are crimped under predetermined temperature and pressure conditions to thereby form a laminated body (step S4). Specifically, crimping is performed by stacking and holding the green sheets as a target of lamination on a predetermined lamination jig, which is not illustrated, while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be determined appropriately to achieve good lamination.

After the laminated body is obtained as described above, the laminated body is cut at a plurality of locations into individual units (referred to as element bodies) of the sensor elements 101 (step S5).

The element bodies obtained by cutting are each fired at a firing temperature of approximately 1300° C. to 1500° C. (step S6). The sensor element 101 is thereby manufactured. That is to say, the sensor element 101 is generated by integrally firing the solid electrolyte layers and the electrodes. The firing temperature in this case is preferably 1200° C. or more and 1500° C. or less (e.g., 1400° C.). Integral firing is performed in this manner, so that the electrodes each have sufficient adhesion strength in the sensor element 101.

The sensor element 101 thus obtained is housed in a predetermined housing, and built into the body (not illustrated) of the gas sensor 100.

<Method for Forming Measurement Electrode>

As described above, in the present embodiment, the measurement electrode 44 having a two-layer configuration as described above is provided in the sensor element 101. Formation of the measurement electrode 44 will be described.

Figure 6:
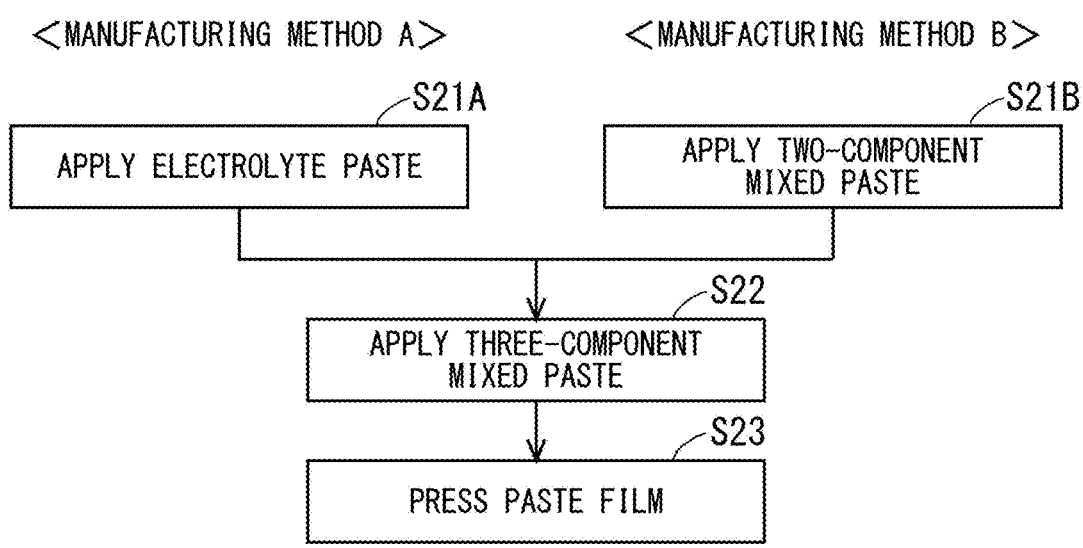
FIG. 6 is a diagram showing procedures for forming a pattern to eventually be the measurement electrode 44.

FIG. 6 is a diagram showing procedures for forming a pattern to eventually be the measurement electrode 44. There are two methods for forming the pattern to be the measurement electrode 44: a manufacturing method A, and a manufacturing method B.

In the manufacturing method A, an electrolyte paste containing, as a ceramic component, zirconia as with the green sheets is first applied at a location, on an upper surface of a green sheet to form the first solid electrolyte layer 4, as a target of formation of the measurement electrode 44 (step S21A). The electrolyte paste is a paste obtained by mixing powder of zirconia as the solid electrolyte and an organic component including a binder and the like.

Then, a three-component mixed paste is superimposedly applied onto an applied film formed by application of the electrolyte paste (step S22). The three-component mixed paste is herein a paste obtained by mixing powder of the noble metal containing Pt as the main component, powder of zirconia as the ceramic component, powder of a pore forming material as a sublimable material to form the pore CV in the measurement electrode 44 eventually formed, and an organic component including a binder and the like.

When application of the three-component mixed paste is completed, a paste applied film (paste-doubled film) where the electrolyte paste and the three-component mixed paste are superimposed is pressed by a predetermined pressing means (step S23). By pressing, some of particles of the noble metal and the pore forming material included in the applied film of the three-component mixed paste enter into the applied film of the electrolyte paste.

After that, when firing targeted for an element body is performed as described above, the paste-doubled film is also fired, and volatilization of the organic component and, further, sintering of the noble metal NM and the solid electrolyte SE progress. In this case, the solid electrolyte in the electrolyte paste is integrated with the solid electrolyte in the green sheet, and a portion in which some particles of the noble metal have entered into the electrolyte paste becomes the lower layer 44L with the progress of sintering. On the other hand, in a portion in which the three-component mixed paste is applied, the pore forming material sublimates with the progress of sintering of the noble metal NM and the solid electrolyte SE to form the pore CV, and the upper layer 44U in which the noble metal NM, the solid electrolyte SE, and the pore CV coexist is eventually obtained. As a result, the measurement electrode 44 having a two-layer configuration as shown in FIG. 2 is formed.

Application thicknesses and application areas of the electrolyte paste and the three-component mixed paste are only required to be set by taking into account contraction by firing and entry of the particles of the noble metal and the pore forming material by pressing so that the thicknesses of the upper layer 44U and the lower layer 44L of the measurement electrode 44 eventually formed and a planar area of the measurement electrode 44 have desired values. For example, a relationship between the application thicknesses and the application areas of the electrolyte paste and the three-component mixed paste and the thicknesses of the upper layer 44U and the lower layer 44L of the measurement electrode 44 and the planar area of the measurement electrode 44 may experimentally be identified in advance. A mixing ratio of the powder of the noble metal, the powder of zirconia as the solid electrolyte, and the powder of the pore forming material of the three-component mixed paste is only required to be set by taking into account entry of the particles of the noble metal and the pore forming material by pressing so that the volume ratios of the noble metal NM, the solid electrolyte SE, and the pore CV in the upper layer 44U (three-phase region) of the measurement electrode 44 eventually formed have desired values.

On the other hand, in the manufacturing method B, a two-component mixed paste is applied at the location, on the upper surface of the green sheet to form the first solid electrolyte layer 4, as the target of formation of the measurement electrode 44 (step S21B). The two-component mixed paste is herein a paste obtained by mixing the powder of the noble metal containing Pt as the main component, the powder of zirconia as the ceramic component, and an organic component including a binder and the like.

Hereinafter, the three-component mixed paste is superimposedly applied onto an applied film formed by application of the two-component mixed paste (step S22), and, further, a paste applied film (paste-doubled film) where the two-component mixed paste and the three-component mixed paste are superimposed is pressed by a predetermined pressing means (step S23), as in the manufacturing method A.

Also in a case of the manufacturing method B, some of particles of the noble metal and the pore forming material included in the coating of the three-component mixed paste enter into the coating of the two-component mixed paste by pressing.

After that, when firing targeted for the element body is performed as described above, the paste-doubled film is also fired, and volatilization of the organic component and, further, sintering of the noble metal NM and the solid electrolyte SE progress. A portion in which the two-component mixed paste is applied thus becomes the lower layer. On the other hand, in the portion in which the three-component mixed paste is applied, the pore forming material sublimates with the progress of sintering of the noble metal NM and the solid electrolyte SE to form the pore CV, and the upper layer 44U in which the noble metal NM, the solid electrolyte SE, and the pore CV coexist is eventually obtained. Also in this case, as a result, the measurement electrode 44 having a two-layer configuration as shown in FIG. 2 is formed.

Also in the case of the manufacturing method B, the application thicknesses and the application areas of the two-component mixed paste and the three-component mixed paste are only required to be set by taking into account contraction by firing and entry of the particles of the noble metal and the pore forming material by pressing so that the thicknesses of the upper layer 44U and the lower layer 44L of the measurement electrode 44 eventually formed and the planar area of the measurement electrode 44 have desired values. A mixing ratio of the powder of the noble metal and the powder of zirconia as the solid electrolyte of the two-component mixed paste is only required to be set by taking into account entry of the particles of the noble metal and the pore forming material by pressing so that the volume ratios of the noble metal NM and the solid electrolyte SE in the lower layer 44L (two-phase region) of the measurement electrode 44 eventually formed have desired values. Similarly, the mixing ratio of the powder of the noble metal, the powder of zirconia as the solid electrolyte, and the powder of the pore forming material of the three-component mixed paste is only required to be set by taking into account entry of the particles of the noble metal and the pore forming material by pressing so that the volume ratios of the noble metal NM, the solid electrolyte SE, and the pore CV in the upper layer 44U (three-phase region) of the measurement electrode 44 eventually formed have desired values. As in the case of the manufacturing method A, the relationship among these values may experimentally be identified in advance.

As described above, according to the present embodiment, the measurement electrode of the sensor element of the limiting current gas sensor is provided to have the two-layer configuration despite that it is provided as the porous cermet electrode as a whole, including the lower layer in which only the noble metal and the solid electrolyte are present and the pore is not present and the upper layer in which the noble metal, the solid electrolyte, and the pore coexist, and thereby the region boundary variation degree as for the region formed of the solid electrolyte and the region occupied by the noble metal and the pore has a large value, so that deterioration of the measurement electrode due to the presence of the surplus oxygen not taken into the measurement electrode is suitably suppressed. A gas sensor in which deterioration of measurement sensitivity is suitably suppressed even if the gas sensor is used continuously is thereby achieved.

<Modifications>

A configuration used in the measurement electrode 44 in the above-mentioned embodiment in which the measurement electrode 44 has the two-layer configuration including the region where the pore is not present and the region where the pore is present, and thereby the region boundary variation degree as for the region formed of the solid electrolyte and the region occupied by the noble metal and the pore has a large value may be applied to the inner pump electrode 22 and the auxiliary pump electrode 51 each provided as a cermet of the Au—Pt alloy and $ZrO_2$ as with the measurement electrode 44. In this case, a separation suppressive effect associated with the anchoring effect can also be obtained in these electrodes. The inner pump electrode 22 and the auxiliary pump electrode 51 having such a configuration can be formed by a similar process to the measurement electrode 44.

Although the two methods, that is, the manufacturing method A and the manufacturing method B, are shown in the above-mentioned embodiment as the method for forming the pattern to be the measurement electrode 44, a manufacturing method C may be used in place of these methods.

In the manufacturing method C, the electrolyte paste used in the manufacturing method A, the two-component mixed paste used in the manufacturing method B, and the three-component mixed paste used in the manufacturing method A and the manufacturing method B are applied in the stated order at the location, on the upper surface of the green sheet to form the first solid electrolyte layer 4, as the target of formation of the measurement electrode 44, and then are pressed by a predetermined pressing means.

Also in a case of the manufacturing method C, the application thicknesses and the application areas of the electrolyte paste, the two-component mixed paste, and the three-component mixed paste are only required to be set by taking into account contraction by firing and entry of the particles of the noble metal and the pore forming material by pressing so that the thicknesses of the upper layer 44U and the lower layer 44L of the measurement electrode 44 eventually formed and the planar area of the measurement electrode 44 have desired values. The mixing ratio of the powder of the noble metal and the powder of zirconia as the solid electrolyte of the two-component mixed paste is only required to be set by taking into account entry of the particles of the noble metal and the pore forming material by pressing so that the volume ratios of the noble metal NM and the solid electrolyte SE in the lower layer 44L (two-phase region) of the measurement electrode 44 eventually formed have desired values. Similarly, the mixing ratio of the powder of the noble metal, the powder of zirconia as the solid electrolyte, and the powder of the pore forming material of the three-component mixed paste is only required to be set by taking into account entry of the particles of the noble metal and the pore forming material by pressing so that the volume ratios of the noble metal NM, the solid electrolyte SE, and the pore CV in the upper layer 44U (three-phase region) of the measurement electrode 44 eventually formed have desired values. As in the case of the manufacturing method A and the manufacturing method B, the relationship among these values may experimentally be identified in advance.

EXAMPLES

Six types of gas sensors 100 (Examples 1 to 6) differing in conditions for manufacturing the measurement electrode 44 were manufactured as examples, and, for each of the obtained gas sensors 100, volume ratios of respective phases (the noble metal, the solid electrolyte, and the pore) in each of the upper layer 44U and the lower layer 44L of the measurement electrode 44 and the region boundary variation degree were evaluated. A continuous drive test in air was also conducted to evaluate a degree of deterioration of the measurement electrode with continued use.

At formation of the measurement electrodes 44, the measurement electrodes 44 were manufactured by two different manufacturing methods, that is, the manufacturing method A and the manufacturing method B, and, for each of the manufacturing methods, the three-component mixed pastes to mainly form the upper layers 44U had two different weight ratios of the powder of the noble metal, the powder of the solid electrolyte, and the pore forming material. One type of the electrolyte paste was used in the manufacturing method A, and one type of the two-component mixed paste was used in the manufacturing method B.

A gas sensor including the measurement electrode 44Z formed using the three-component mixed paste as a whole was also manufactured as a conventional example (a method for manufacturing the gas sensor is hereinafter referred to as a conventional manufacturing method), and, for the manufactured gas sensor, the volume ratios of the respective phases (the noble metal, the solid electrolyte, and the pore) of the measurement electrode 44Z were evaluated, and the continuous drive test in air was conducted as with the gas sensors of the examples.

Weight ratios (component ratios) of the powder of the noble metal, the powder of the solid electrolyte, and the pore forming material of the pastes used to manufacture the measurement electrodes 44 of Examples 1 to 6 and the measurement electrode 44Z of the conventional example are shown in Table 1 as a list.

TABLE 1

| | | MEASUREMENT ELECTRODE PASTE COMPONENT RATIOS (WEIGHT RATIOS) | | | | |
|---|---|---|---|---|---|---|
| | MEASUREMENT | FOR UPPER LAYER FORMATION (a:b:c) | | | FOR LOWER LAYER FORMATION (d:e) | |
| | ELECTRODE FORMATION METHOD | NOBLE METAL a | ELECTROLYTE b | PORE FORMING MATERIAL c | USED PASTE | NOBLE METAL d | ELECTROLYTE e |
| CONVENTIONAL EXAMPLE | CONVENTIONAL MANUFACTURING METHOD | 10 | 2 | 1 | NOT USED | — | — |

TABLE 1-continued

| | | MEASUREMENT ELECTRODE PASTE COMPONENT RATIOS (WEIGHT RATIOS) | | | | | |
|---|---|---|---|---|---|---|---|
| | MEASUREMENT | FOR UPPER LAYER FORMATION (a:b:c) | | | FOR LOWER LAYER FORMATION (d:e) | | |
| | ELECTRODE FORMATION METHOD | NOBLE METAL a | ELECTROLYTE b | PORE FORMING MATERIAL c | USED PASTE | NOBLE METAL d | ELECTROLYTE e |
| EXAMPLE 1 | MANUFACTURING METHOD A | 10 | 2 | 1 | ELECTROLYTE PASTE | — | 10 |
| EXAMPLE 2 | MANUFACTURING METHOD A | 30 | 10 | 1 | | — | 10 |
| EXAMPLE 3 | MANUFACTURING METHOD A | 30 | 10 | 1 | | — | 10 |
| EXAMPLE 4 | MANUFACTURING METHOD B | 10 | 2 | 1 | TWO-COMPONENT MIXED PASTE | 5 | 1 |
| EXAMPLE 5 | MANUFACTURING METHOD B | 30 | 10 | 1 | | 5 | 1 |
| EXAMPLE 6 | MANUFACTURING METHOD B | 10 | 2 | 1 | | 5 | 1 |

In Table 1, weight ratios of the three-component mixed pastes are shown in columns "FOR UPPER LAYER FORMATION", and weight ratios of the electrolyte pastes and weight ratios of the two-component mixed pastes are shown in columns "FOR LOWER LAYER FORMATION".

When a, b, and c are respectively weight ratios of the powder of the noble metal, the powder of the solid electrolyte, and the pore forming material of the three-component mixed pastes, and d and e are respectively weight ratios of the powder of the noble metal and the powder of the solid electrolyte of the two-component mixed pastes, the weight ratios of the three-component mixed pastes satisfy an equation a:b:c=10:2:1 (Examples 1, 4, and 6) or an equation a:b:c=30:10:1 (Examples 2, 3, and 5) as shown in Table 1. When the mixing ratio c of the pore forming material of each of the three-component mixed pastes is one, the two-component mixed pastes satisfy an equation (c:)d:e=(1:)5:1 (Examples 4, 5, and 6). Furthermore, as for the weight ratio of the powder of the solid electrolyte of each of the electrolyte pastes, which is expressed as e for the sake of convenience, relative to the mixing ratio c of the pore forming material of each of the three-component mixed pastes, an equation c:e=1:10 (Examples 1 and 2) is satisfied.

In each of Examples 1 to 3 in which the measurement electrode 44 is formed by the manufacturing method A, an intended application thickness of the electrolyte paste is 10 μm, and an intended application thickness of the three-component mixed paste is 15 μm.

In each of Examples 4 to 6 in which the measurement electrode 44 is formed by the manufacturing method B, an intended application thickness of the two-component mixed paste is 5 μm, and the intended application thickness of the three-component mixed paste is 15 μm.

In the conventional example in which the measurement electrode 44Z is manufactured by the conventional manufacturing method, the three-component mixed paste satisfies the equation a:b:c=10:2:1, and the intended application thickness of the three-component mixed paste is 15 μm.

The volume ratios of the respective phases in each of the upper layer 44U and the lower layer 44L of the measurement electrode 44 and results of evaluation of the region boundary variation degree in each of the examples and the conventional example are shown in Table 2. The volume ratios in the measurement electrode 44Z of the conventional example are shown in a column "UPPER LAYER" for the sake of convenience.

TABLE 2

| | MEASUREMENT ELECTRODE VOLUME RATIOS (%): IN RELATION TO EACH LAYER AS A WHOLE AS 100% | | | | | ELECTROLYTE BOUNDARY LOCATION VARIATION | |
|---|---|---|---|---|---|---|---|
| | UPPER LAYER (THREE-PHASE REGION) | | | LOWER LAYER (TWO-PHASE REGION) | | AVERAGE | STANDARD |
| | NOBLE METAL P1 | ELECTROLYTE P2 | PORE P3 | NOBLE METAL P4 | ELECTROLYTE P5 | VALUE (μm) | DEVIATION σ (μm) |
| CONVENTIONAL EXAMPLE | 40 | 20 | 40 | — | — | 0 | 0 |
| EXAMPLE 1 | 40 | 20 | 40 | 40 | 60 | 1.0 | 1.1 |
| EXAMPLE 2 | 45 | 40 | 15 | 45 | 55 | 2.1 | 1.9 |
| EXAMPLE 3 | 45 | 40 | 15 | 45 | 55 | 0.4 | 0.5 |
| EXAMPLE 4 | 40 | 20 | 40 | 40 | 60 | 4.9 | 5.0 |
| EXAMPLE 5 | 45 | 40 | 15 | 40 | 60 | 2.5 | 2.6 |
| EXAMPLE 6 | 40 | 20 | 40 | 40 | 60 | 6.1 | 6.3 |

In Table 2, P1(%), P2(%), and P3(%) are respectively the volume ratios of the noble metal NM, the solid electrolyte SE, and the pore CV in the upper layer 44U, and P4(%) and P5(%) are respectively the volume ratios of the noble metal NM and the solid electrolyte SE in the lower layer 44L. An equation P1+P2+P3=P4+P5=100(%) is satisfied.

The volume ratios of the respective phases in each of the measurement electrodes 44 and the measurement electrode 44Z were obtained by capturing a cross-sectional SEM image of the electrode, and performing known image processing on the cross-sectional SEM image. The cross-sectional SEM image was generally ternary valued so that the region where the noble metal NM was present was white, the region where the solid electrolyte SE was present was gray, and the region where the pore or the internal space was present was black, and ratios of the areas (ratios of the cross-sectional areas) of the respective regions were set to the volume ratios. The region boundary variation degree was evaluated by measuring, from the SEM image of the cross section including the first solid electrolyte layer 4 and the measurement electrode 44 and perpendicular to the thickness direction of the sensor element, distances from the boundary of the first region and the second region to the lowermost end of the range in which the noble metal NM was present at intervals of 0.1 μm in the longitudinal direction of the element, and determining the average value and the standard deviation a thereof. A value of the standard deviation a corresponds to the region boundary variation degree. The average value and the standard deviation a in the conventional example were both set to zero.

The results shown in Table 2 indicate that the measurement electrode 44 has the two-layer configuration including the upper layer 44U and the lower layer 44L in each of Examples 1 to 6.

More particularly, values of P1, P2, P3, P4, and P5 are the same in Examples 1, 4, and 6, which differ in the method for manufacturing the measurement electrode 44, but have in common that the weight ratios of the three-component mixed pastes satisfy the equation a:b:c=10:2:1. From among these values, the volume ratio of the noble metal NM in each of the upper layer 44U and the lower layer 44L satisfies an equation P1=P4=40%. As for the volume ratio of the solid electrolyte SE, the value of P2 in the upper layer 44U is 20%, whereas the value of P5 in the lower layer 44L is 60%, which is greater than the value of P2.

In contrast, in Examples 2, 3, and 5, which differ in the method for manufacturing the measurement electrode 44, but have in common that the weight ratios of the three-component mixed pastes satisfy the equation a:b:c=30:10:1, the values of P1, P2, and P3 are the same, but the values of P4 and P5 in Examples 2 and 3 differ from those in Example 5 by 5%. That is to say, the volume ratio P1 of the noble metal NM in the upper layer 44U has a value of 45%, and the volume ratio P2 of the solid electrolyte SE in the upper layer 44U has a value of 40% in each of Examples 2, 3, and 5, but the volume ratio P4 of the noble metal NM in the lower layer 44L has a value of 45% in each of Examples 2 and 3, and has a value of 40% in Example 5. In response to these values, the volume ratio P5 of the solid electrolyte SE has a value of 55% in each of Examples 2 and 3, and has a value of 60% in Example 5.

In each of the examples, however, the volume ratio of the solid electrolyte SE in the lower layer 44L is greater than the volume ratio of the solid electrolyte SE in the upper layer 44U. Specifically, the volume ratio of the solid electrolyte SE in the upper layer 44U is in a range of 20% to 40%, and the volume ratio of the solid electrolyte SE in the lower layer 44L is in a range of 50% to 60%.

The volume ratios P1, P2, and P3 of the respective phases in the measurement electrode 44Z of the conventional example are the same as those of Examples 1 and 4 in each of which the three-component mixed paste having the same weight ratios is used.

The standard deviation σ corresponding to the region boundary variation degree has a greater value in each of Examples 4 to 6 manufactured by the manufacturing method B than in each of Examples 1 to 3 manufactured by the manufacturing method A. Examples (Examples 2 and 3, and Examples 4 and 6) having the manufacturing method and the weight ratios in the three-component mixed paste in common, however, differ in value of the standard deviation σ, and a correspondence relationship between the weight ratios and the value of the standard deviation σ varies depending on the manufacturing method.

The continuous drive test in air was conducted by continuously operating each of the gas sensors in an air atmosphere at 25±5° C. for 3000 hours, and measuring values of the NOx current (also referred to as NOx output) at the start of operation, after the elapse of 1000 hours, after the elapse of 2000 hours, and after the elapse of 3000 hours. The rate of change of the NOx current at each measurement time to a value of the NOx current at the start of operation was calculated as a NOx output change rate. The NOx output change rate is a value indicative of a degree of deterioration of each of the measurement electrodes 44 and the measurement electrode 44Z.

FIG. 7 is a graph showing results of the continuous drive test. In FIG. 7, a horizontal axis represents a drive time, and a vertical axis represents the NOx output change rate.

As shown in FIG. 7, in the gas sensor of the conventional example, the NOx output significantly changes over the drive time, and the NOx output change rate taking into account variation is approximately 11.5±3.5% after the elapse of 3000 hours, whereas, in the gas sensor of each of Examples 1 to 6, the NOx output change rate remains at most at approximately 6% even after the elapse of 3000 hours. This means that deterioration of the measurement electrode is suppressed even after the elapse of 3000 hours in the gas sensor of each of Examples 1 to 6.

In particular, in the gas sensor of each of examples other than Example 3, the NOx output change rate generally remains at 3% or less after the elapse of 3000 hours, and it is determined that deterioration of the measurement electrode is more suitably suppressed in the gas sensor.

The above-mentioned results of the continuous drive test indicate that, when the measurement electrode of the sensor element of the limiting current type gas sensor is provided to have the two-layer configuration including the lower layer having the two-phase configuration of the noble metal and the solid electrolyte and the upper layer having the three-phase configuration of the noble metal, the solid electrolyte, and the pore, and thereby the region boundary variation degree has a large value, deterioration of the measurement electrode when the gas sensor is used continuously can be suppressed.

While the invention has been shown and described in detail, the foregoing description is in all aspects illustrative and not restrictive. It is therefore understood that numerous modifications and variations can be devised without departing from the scope of the invention.

What is claimed is:

1. A sensor element of a limiting current type NOx sensor, the sensor element comprising:
   a base part containing an oxygen-ion conductive solid electrolyte as a constituent material;
   a measurement internal space into which a measurement gas having an oxygen concentration adjusted in advance is introduced; and
   at least one pump cell including a measurement electrode disposed in the measurement internal space, an out-of-space pump electrode disposed at a location other than the measurement internal space, and a portion of the base part located between the measurement electrode and the out-of-space pump electrode, wherein the measurement electrode includes a noble metal, the oxygen-ion conductive solid electrolyte material, and pores, and includes:
- an upper layer consisting of the noble metal, the oxygen-ion conductive solid electrolyte material, and the pores; and
- a lower layer consisting of the noble metal and the oxygen-ion conductive solid electrolyte material, in the measurement electrode, a region boundary variation degree being a degree of variation of a boundary between a first region and a second region in a thickness direction of the sensor element is 0.5 µm or more and 6.5 µm or less, the first region being formed of the base part and the oxygen-ion conductive solid electrolyte material contiguous with the base part, the second region being occupied by the noble metal and the pores, a volume ratio of the oxygen-ion conductive solid electrolyte material in the upper layer is 20% to 40%, and a volume ratio of the oxygen-ion conductive solid electrolyte material in the lower layer is 50% to 60%.

2. The sensor element of the NOx sensor according to claim 1, wherein
a ratio of a thickness of the upper layer to a thickness of the lower layer is in a range of 95:5 to 10:90.

3. The sensor element of the NOx sensor according to claim 2, wherein
the ratio of the thickness of the upper layer to the thickness of the lower layer is in a range of 90:10 to 30:70.

4. The sensor element of the NOx sensor according to claim 3, wherein
the region boundary variation degree is 1 µm or more and 5 µm or less.

5. The sensor element of the NOx sensor according to claim 2, wherein the region boundary variation degree is 1 µm or more and 5 µm or less.

6. The sensor element of the NOx sensor according to claim 1, wherein
the region boundary variation degree is 1 µm or more and 5 µm or less.

* * * * *